US012564387B2

(12) United States Patent
Nishiura et al.

(10) Patent No.: US 12,564,387 B2
(45) Date of Patent: Mar. 3, 2026

(54) ULTRASOUND DIAGNOSTIC APPARATUS AND ULTRASOUND DIAGNOSTIC SYSTEM

(71) Applicant: FUJIFILM Corporation, Tokyo (JP)

(72) Inventors: Tomofumi Nishiura, Tokyo (JP);
Tsuyoshi Matsumoto, Tokyo (JP);
Tomoki Inoue, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 18/817,171

(22) Filed: Aug. 27, 2024

(65) Prior Publication Data

US 2025/0072874 A1 Mar. 6, 2025

(30) Foreign Application Priority Data

Aug. 30, 2023 (JP) ................................. 2023-139756

(51) Int. Cl.
*A61B 8/00* (2006.01)
*G16H 30/40* (2018.01)
*G16H 50/20* (2018.01)

(52) U.S. Cl.
CPC ............... *A61B 8/54* (2013.01); *G16H 30/40* (2018.01); *G16H 50/20* (2018.01)

(58) Field of Classification Search
CPC ........... A61B 8/54; A61B 8/5223; A61B 8/13; A61B 8/52; G16H 30/40; G16H 50/20; G06T 7/0012
See application file for complete search history.

(56) References Cited

U.S. PATENT DOCUMENTS 5,873,824 A 2/1999 Doi et al.
10,918,360 B2 2/2021 Imai 11,389,139 B2 7/2022 Yang et al.
11,682,491 B2 6/2023 Nagai et al.
2018/0285643 A1 10/2018 Nakano et al.
2020/0161005 A1* 5/2020 Lyman ................... G16H 15/00
2021/0212660 A1 7/2021 Nishiura

FOREIGN PATENT DOCUMENTS

JP H10171910 6/1998
JP 6423540 11/2018
JP 2018169746 11/2018
JP 2020204970 12/2020
JP 2021506470 2/2021
JP 2021108842 8/2021

OTHER PUBLICATIONS

Zhou et al., "Learning Deep Features for Discriminative Localization", arxiv Dec. 2015, 1512.04150, pp. 1-10.
Selvaraju et al., "Grad-CAM: Visual Explanations from Deep Networks via Gradient-based Localization", arxiv Oct. 2016, 1610. 02391, pp. 1-23.

* cited by examiner

*Primary Examiner* — Amal Aly Farag

(74) *Attorney, Agent, or Firm* — JCIPRNET

(57) ABSTRACT

An evaluation unit evaluates performance of an analytic model (internal analytic model) based on internal data extracted from the analytic model and output data of the analytic model. A determination unit determines use of an external analytic model based on an evaluation result of the evaluation unit. In that case, an input image (tomographic image) is sent to an information processing apparatus via a communication unit. An analysis result of the analytic model (external analytic model) is sent to a calculation control unit via the communication unit.

9 Claims, 13 Drawing Sheets

FIG. 3

| | INTERNAL ANALYTIC MODEL | EXTERNAL ANALYTIC MODEL |
|---|---|---|
| EXAMINATION SITE | (A1) SPECIFIC EXAMINAATION SITE | (B1) ALL EXAMINAATION SITES |
| NUMBER OF IDENTIFIABLE CROSS SECTIONS | (A2) RELATIVELY SMALL NUMBER | (B2) LARGE NUMBER |
| AMOUNT OF TRAINING | (A3) RELATIVELY SMALL AMOUNT | (B3) LARGE AMOUNT |
| ... | ... | ... |
| RESPONSIVENESS | (A4) HIGH-SPEED | (B4) (DEPENDING ON SITUATION) |

Figure 12:
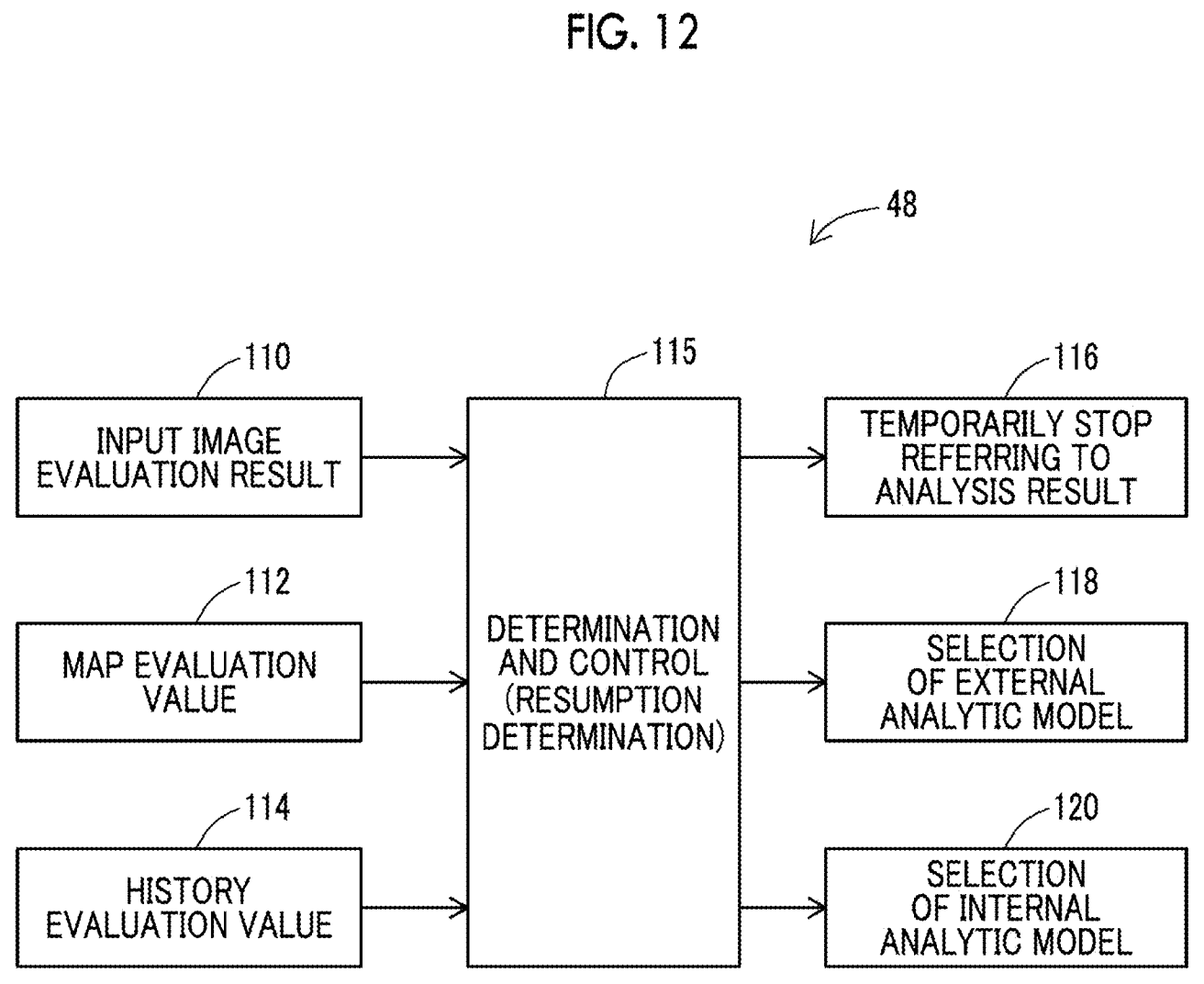

110 INPUT IMAGE EVALUATION RESULT

112 MAP EVALUATION VALUE

114 HISTORY EVALUATION VALUE

115 DETERMINATION AND CONTROL (RESUMPTION DETERMINATION)

116 TEMPORARILY STOP REFERRING TO ANALYSIS RESULT

118 SELECTION OF EXTERNAL ANALYTIC MODEL

120 SELECTION OF INTERNAL ANALYTIC MODEL

FIG. 13

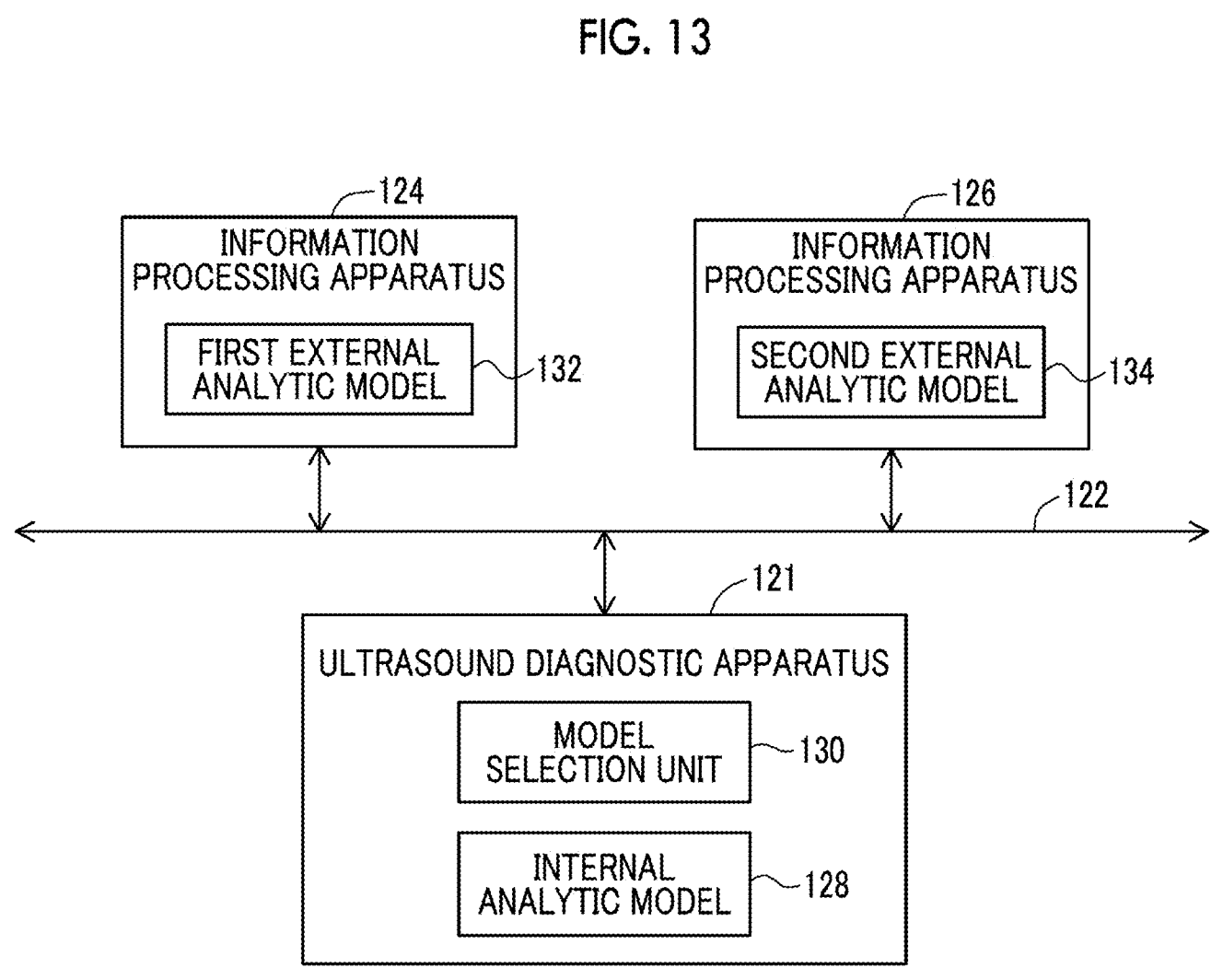

126 — INFORMATION PROCESSING APPARATUS

SECOND EXTERNAL ANALYTIC MODEL — 134

124 — INFORMATION PROCESSING APPARATUS

FIRST EXTERNAL ANALYTIC MODEL — 132

122

121

ULTRASOUND DIAGNOSTIC APPARATUS

MODEL SELECTION UNIT — 130

INTERNAL ANALYTIC MODEL — 128

ULTRASOUND DIAGNOSTIC APPARATUS AND ULTRASOUND DIAGNOSTIC SYSTEM

CROSS-REFERENCE TO RELATED APPLICATION

This application claims the priority benefit of Japan application serial no. 2023-139756, filed on Aug. 30, 2023. The entirety of the above-mentioned patent application is hereby incorporated by reference herein and made a part of this specification.

BACKGROUND OF THE INVENTION

1. Field of the Invention

The present disclosure relates to an ultrasound diagnostic apparatus and an ultrasound diagnostic system, and particularly, to a technique of selectively using a plurality of analytic models.

2. Description of the Related Art

An ultrasound diagnostic apparatus is used in an ultrasound examination. Some ultrasound diagnostic apparatuses comprise an analytic model (a model generated through a machine learning process) that analyzes an ultrasound image. As such an analytic model, a model that identifies a type of a tomographic image, a model that detects a lesion part in the tomographic image, a model that analyzes the lesion part in the tomographic image, and the like are known. The analytic model is constructed on, for example, a convolutional neural network (CNN).

JP6423540B describes an ultrasound diagnostic apparatus comprising an analytic model that identifies a type of a tomographic image. JP2020-204970A describes an ultrasound diagnostic apparatus comprising a plurality of analytic models.

Zhou et al., Learning Deep Features for Discriminative Localization, arxiv 2015, 1512.04150 and Selvaraju et al., Grad-CAM: Visual Explanations from Deep Networks via Gradient-based Localization, arxiv 2016, 1610.02391 describe a technique of generating a class activation map based on internal data extracted from a CNN. The class activation map is a map representing a reaction distribution of the CNN and is also referred to as a saliency map (or a heat map).

SUMMARY OF THE INVENTION

Because of various structural or operational constraints, it may not be possible to provide a high-performance analytic model inside the ultrasound diagnostic apparatus. Alternatively, it is also conceivable to provide an analytic model having higher performance after the start of use of the ultrasound diagnostic apparatus provided with the analytic model. It is desired to implement a mechanism that temporarily or supplementarily uses an analytic model (external analytic model) provided outside the ultrasound diagnostic apparatus in a situation in which the analytic model (internal analytic model) provided inside the ultrasound diagnostic apparatus is not sufficiently functioning.

JP6423540B and JP2020-204970A described above do not describe a configuration for using the analytic model provided outside the ultrasound diagnostic apparatus.

An object of the present disclosure is to provide an ultrasound diagnostic apparatus provided with a mechanism for selectively using an internal analytic model and an external analytic model. Alternatively, the object of the present disclosure is to provide an ultrasound diagnostic apparatus provided with a function of using the external analytic model in a case where use of the internal analytic model is not appropriate.

According to the present disclosure, there is provided an ultrasound diagnostic apparatus used in an ultrasound examination of a subject, the ultrasound diagnostic apparatus comprising: a generator that generates an ultrasound image based on data obtained from the subject; an internal analytic model that is provided inside the ultrasound diagnostic apparatus and analyzes the ultrasound image; an evaluator that evaluates the internal analytic model; a determiner that determines use of an external analytic model provided outside the ultrasound diagnostic apparatus, based on an evaluation result of the evaluator; and a communicator that transfers the ultrasound image to the external analytic model in a case where the use of the external analytic model has been determined, and that receives an analysis result of the external analytic model.

According to the present disclosure, there is provided an ultrasound diagnostic system comprising: an ultrasound diagnostic apparatus used in an ultrasound examination of a subject; and an information processing apparatus connected to the ultrasound diagnostic apparatus via a network, in which the information processing apparatus includes an external analytic model that analyzes an ultrasound image outside the ultrasound diagnostic apparatus, and the ultrasound diagnostic apparatus includes a generator that generates the ultrasound image based on data obtained from the subject, an internal analytic model that analyzes the ultrasound image inside the ultrasound diagnostic apparatus, an evaluator that evaluates the internal analytic model, a determiner that determines use of the external analytic model, based on an evaluation result of the evaluator, and a communicator that transfers the ultrasound image to the external analytic model in a case where the use of the external analytic model has been determined, and that receives an analysis result of the external analytic model.

According to the present disclosure, the internal analytic model and the external analytic model can be selectively used. Alternatively, according to the present disclosure, the external analytic model can be used in a case where the use of the internal analytic model is not appropriate.

BRIEF DESCRIPTION OF THE DRAWINGS

FIG. 3 is a diagram showing a difference between an internal analytic model and an external analytic model.

FIG. 5 is a diagram showing an example of a saliency map generation method.

FIG. 12 is a diagram showing an operation example of a determination unit.

FIG. 13 is a block diagram showing an ultrasound diagnostic system according to another embodiment.

DESCRIPTION OF THE PREFERRED EMBODIMENTS

Figure 1:
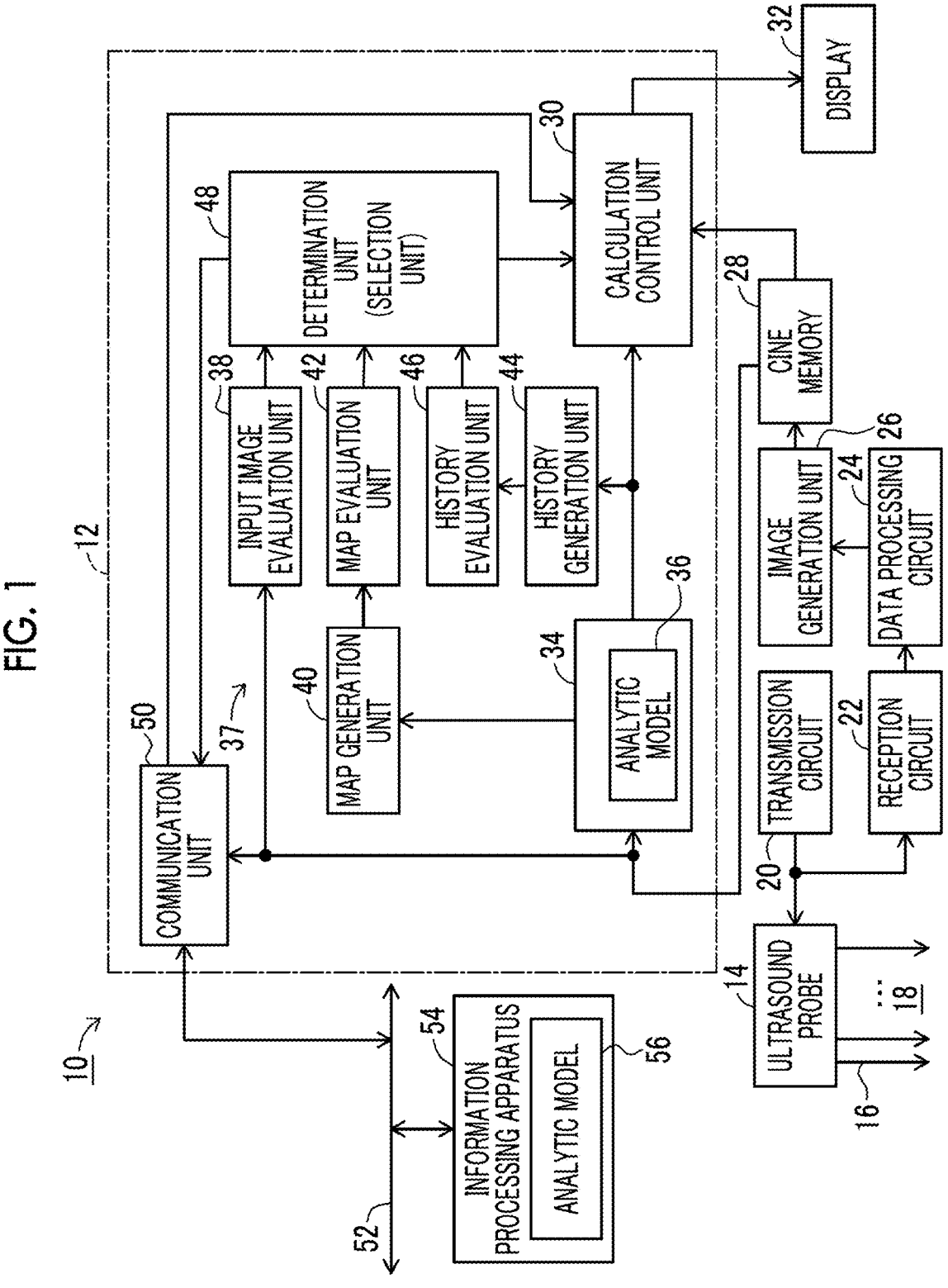
FIG. 1 is a block diagram showing an ultrasound diagnostic system according to an embodiment.

Hereinafter, embodiments will be described with reference to the drawings.

(1) Outline of Embodiment

An ultrasound diagnostic apparatus according to an embodiment is an ultrasound diagnostic apparatus used in an ultrasound examination of a subject, and includes a generator, an internal analytic model, an evaluator, a determiner, and a communicator. The generator generates an ultrasound image based on data obtained from the subject. The internal analytic model is provided inside the ultrasound diagnostic apparatus and analyzes the ultrasound image. The evaluator evaluates the internal analytic model. The determiner determines use of an external analytic model provided outside the ultrasound diagnostic apparatus, based on an evaluation result of the evaluator. The communicator transfers the ultrasound image to the external analytic model in a case where the use of the external analytic model has been determined, and receives an analysis result of the external analytic model.

With the above-described configuration, in a case where the use of the internal analytic model is not adequate, the external analytic model is used instead of the internal analytic model. That is, it is possible to use the external analytic model as necessary while prioritizing the use of the internal analytic model.

Some or all of evaluation units to be described below correspond to the above-described evaluator. A determination unit to be described below corresponds to the above-described determiner. A communication unit to be described below corresponds to the above-described communicator. The internal analytic model and the external analytic model are each a model generated through a machine learning process. In general, the performance of the external analytic model is higher than the performance of the internal analytic model.

In the embodiment, the evaluator evaluates the internal analytic model based on at least one of internal data extracted from the internal analytic model or output data output from the internal analytic model. The internal data is data in which an analysis process of the internal analytic model is reflected, and the output data is data representing an analysis result of the internal analytic model. By referring to one or both of the internal data and the output data, it is possible to determine whether or not the internal analytic model is sufficiently functioning in relation to the ultrasound image input to the internal analytic model.

In the embodiment, the evaluator evaluates the internal analytic model based on both the internal data and the output data. With this configuration, it is possible to comprehensively or more accurately determine whether or not the internal analytic model is sufficiently functioning in relation to the ultrasound image input to the internal analytic model.

In the embodiment, the evaluator includes a map generator and a map evaluator. The map generator generates a saliency map based on the plurality of feature maps as the internal data extracted from the internal analytic model. The map evaluator evaluates the saliency map. The determiner determines the use of the external analytic model based on an evaluation result of the saliency map. A map generation unit to be described below corresponds to the above-described map generator, and a map evaluation unit to be described below corresponds to the above-described map evaluator.

The saliency map represents a reaction distribution of the internal analytic model, that is, an activation distribution. Based on the saliency map, a degree of reaction or a reaction aspect of the internal analytic model can be evaluated. For example, a plurality of feature maps are extracted from a plurality of convolutional layers, and the saliency map is generated by weighted addition of the plurality of feature maps.

In the embodiment, the evaluator includes a history generator and a history evaluator. The history generator generates a confidence degree history representing temporal changes of confidence degrees for a plurality of classes, based on the output data output from the internal analytic model. The history evaluator evaluates the confidence degree history. The determiner determines the use of the external analytic model based on an evaluation result of the confidence degree history.

In general, in a case where the internal analytic model is effectively functioning for the input image, only the confidence degree for a specific class is high. On the contrary, in a case where the internal analytic model is not effectively functioning for the input image, the confidence degree for any class is low. Alternatively, the confidence degrees for a plurality of classes are high. By referring to the confidence degree history, the performance of the internal analytic model and the temporal changes thereof can be comprehensively evaluated. In the embodiment, the confidence degree history is composed of a plurality of confidence degree graphs corresponding to the plurality of classes. The plurality of classes are a plurality of classification classes and are, for example, a plurality of cross-section types.

The ultrasound diagnostic apparatus according to the embodiment includes an input image evaluator that evaluates an input image, which is an ultrasound image input to the internal analytic model. The determiner determines the use of the external analytic model based on the evaluation result of the input image. In the embodiment, the determiner determines the use of the external analytic model, in a case where the input image satisfies an image quality condition, and an evaluation result of the internal analytic model does not satisfy a model performance condition. With this configuration, it is possible to correctly determine the use of the external analytic model.

The ultrasound diagnostic apparatus according to the embodiment includes a controller that controls an operation of the ultrasound diagnostic apparatus. The internal analytic model and the external analytic model are each a model that identifies a cross section. The controller controls the operation of the ultrasound diagnostic apparatus based on the cross section identified by the internal analytic model until the use of the external analytic model is determined. Meanwhile, the controller controls the operation of the ultrasound diagnostic apparatus based on the cross section identified by the external analytic model after the use of the external analytic model has been determined. With this configuration, operation control based on a cross-section type is optimized.

For example, an operation condition is switched, the measurement is executed, or a body mark is generated, based on the identified cross section.

In the embodiment, the evaluator continues to evaluate the internal analytic model even after the use of the external analytic model has been determined. The determiner determines resumption of the use of the internal analytic model based on the evaluation result of the evaluator after the use of the external analytic model has been determined. In general, better responsiveness can be obtained by using the internal analytic model. With the above-described configuration, it is possible to prioritize the use of the internal analytic model.

An ultrasound diagnostic system according to the embodiment includes an ultrasound diagnostic apparatus and an information processing apparatus. The information processing apparatus includes an external analytic model that analyzes the ultrasound image outside the ultrasound diagnostic apparatus. The ultrasound diagnostic apparatus includes a generator, an internal analytic model, an evaluator, a determiner, and a communicator. The generator generates the ultrasound image based on data obtained from the subject. The internal analytic model analyzes the ultrasound image inside the ultrasound diagnostic apparatus. The evaluator evaluates the internal analytic model. The determiner determines the use of the external analytic model based on the evaluation result of the evaluator. The communicator transfers the ultrasound image to the external analytic model in a case where the use of the external analytic model has been determined, and receives the analysis result of the external analytic model.

(2) Details of Embodiment

FIG. 1 shows an ultrasound diagnostic apparatus 10 according to the embodiment. This ultrasound diagnostic apparatus 10 is a medical apparatus that is installed in a medical institution such as a hospital and that is used in the ultrasound examination of the subject. The ultrasound diagnostic apparatus 10 includes a processor 12 that functions as an information processing unit. The processor 12 is, for example, a CPU that executes a program. A plurality of functions exhibited by the processor 12 are represented by a plurality of blocks in FIG. 1.

An ultrasound probe 14 is a device that transmits ultrasound waves into a living body and that receives reflected waves from the living body. The ultrasound probe 14 includes a transducer array consisting of a plurality of transducers. The transducer array forms an ultrasound beam 16. A beam scanning plane 18 is formed through electronic scanning of the ultrasound beam 16.

As an electronic scanning method of the ultrasound beam 16, an electronic linear scanning method, an electronic sector scanning method, and the like are known. As the transducer array, a two-dimensional transducer array may be provided. Volume data can be acquired from a three-dimensional space in the living body by performing two-dimensional scanning with the ultrasound beam through the two-dimensional transducer array.

A transmission circuit 20 is an electronic circuit that functions as a transmission beam former, and outputs a plurality of transmission signals to the transducer array in parallel during transmission. As a result, a transmission beam is formed.

A reception circuit 22 is an electronic circuit that functions as a reception beam former, and applies phase addition to a plurality of reception signals output in parallel from the transducer array during reception, thereby generating reception beam data. With the repetition of the electronic scanning, a reception frame data sequence is output from the reception circuit 22. Each piece of the reception frame data is composed of a plurality of pieces of reception beam data arranged in an electronic scanning direction. Each piece of the reception beam data is composed of a plurality of pieces of echo data arranged in a depth direction.

A data processing circuit 24 is a circuit that processes each piece of the reception frame data. The data processing circuit 24 includes a detection circuit, a logarithmic transformation circuit, a filter, and the like.

An image generation unit 26 includes a digital scan converter (DSC). The DSC has a coordinate transformation function, a pixel interpolation function, and the like. A display frame data sequence is generated from the reception frame data sequence by the DSC. In the embodiment, the display frame data sequence corresponds to a tomographic image (B-mode tomographic image) as a moving image. Each individual piece of the display frame data that constitutes the display frame data sequence corresponds to a tomographic image as a still image. An ultrasound image (for example, a blood flow image or an elastography image) other than the tomographic image may be generated.

Following the image generation unit 26, a cine memory 28 is provided. The display frame data sequence is temporarily stored in the cine memory 28. The display frame data sequence read out from the cine memory 28 is sent to a calculation control unit 30. The cine memory 28 has a ring buffer structure. The cine memory 28 is configured with, for example, a semiconductor memory.

The calculation control unit 30 has a function of controlling an operation of each component that constitutes the ultrasound diagnostic apparatus and a function of executing various calculations. In the shown configuration example, the calculation control unit 30 also functions as a display processing unit. The display frame data sequence is sent from the calculation control unit 30 to a display 32. The tomographic image as a moving image is displayed on the display 32. Another ultrasound image may be displayed on the display 32. The display 32 is configured with an organic EL device, a liquid crystal display, or the like. An operation panel (not shown) is connected to the calculation control unit 30.

In a case of performing moving image analysis, the display frame data sequence read out from the cine memory 28 is sent to the image analysis unit 34. In a case of performing still image analysis, specific display frame data stored in the cine memory 28 is sent to the image analysis unit 34. For example, during the real-time operation, the display frame data sequence is sent from the cine memory 28 to the image analysis unit 34, and in a frozen state in which the transmission and reception are stopped by a freeze operation, the specific display frame data is sent from the cine memory 28 to the image analysis unit 34.

The specific display frame data is display frame data corresponding to the still image displayed on the display 32. The specific display frame data is sequentially selected by a user as necessary. Either the moving image analysis or the still image analysis may be selected by the user. In the configuration example shown in FIG. 1, the cine memory 28 is provided between the image generation unit 26 and the calculation control unit 30, but the cine memory 28 may be provided between the data processing circuit 24 and the image generation unit 26. In that case, the reception frame data sequence or the specific reception frame data is sent to the image analysis unit 34.

The image analysis unit 34 includes an analytic model (internal analytic model) 36 as artificial intelligence (AI). The analytic model 36 is a model generated through a machine learning process. In the embodiment, the analytic model 36 is constructed on a convolutional neural network (CNN). The analytic model 36 according to the embodiment is a model that identifies a type of the tomographic image (that is, a cross-section type). Examples of the other analytic models include a model that detects a lesion part included in the tomographic image, and a model that analyzes the lesion part included in the tomographic image. The analysis result of the analytic model 36, that is, output data is sent to the calculation control unit 30.

The calculation control unit 30 controls the operation of the ultrasound diagnostic apparatus based on the cross-section type identified by the analytic model 36. For example, the progress of an examination protocol is controlled based on the identified cross-section type, the measurement suitable for the identified cross-section type is initiated, or a body mark corresponding to the identified cross-section type is selected.

An evaluation unit 37 is a module (evaluator) that evaluates whether or not the analytic model 36 properly exhibits the function for each individual piece of the display frame data (input image) that is input to the analytic model 36. The evaluation unit 37 evaluates the performance of the analytic model 36 for each input image and/or for each series of input images. Specifically, the evaluation unit 37 includes a map generation unit 40, a map evaluation unit 42, a history generation unit 44, and a history evaluation unit 46. In the embodiment, the evaluation unit 37 further includes an input image evaluation unit 38.

The input image evaluation unit 38 is an evaluator that evaluates quality of the input image. The evaluation result of the input image evaluation unit 38 is sent to a determination unit 48. Since it is not reasonable to evaluate the performance of the analytic model 36 in a situation in which the quality of the input image is degraded, that is, in order to correctly evaluate the performance of the analytic model 36, the input image evaluation unit 38 is provided. Details of the input image evaluation method will be described below.

The map generation unit 40 extracts internal data generated or used in an analysis process of the analytic model 36 from the analytic model 36 and generates a saliency map based on the extracted internal data. More specifically, the internal data includes a plurality of feature maps generated by the action of the plurality of convolutional layers. The map generation unit 40 generates the saliency map by performing weighted addition of the plurality of feature maps. The saliency map represents the reaction distribution of the analytic model and is composed of a plurality of intensities (a plurality of activity levels) arranged in two-dimensionally.

The map evaluation unit 42 evaluates whether or not the analysis on the input image is appropriate by evaluating the saliency map. For example, the saliency map is evaluated based on the number of high intensities or the distribution of high intensities in the saliency map. The map evaluation unit 42 calculates a map evaluation value. Details of a map generation method and a map evaluation method will be described below.

The history generation unit 44 generates a confidence degree history based on the output data of the analytic model 36. The output data of the analytic model 36 includes a plurality of confidence degrees (confidence degree sets) corresponding to a plurality of classes (that is, a plurality of identifiable cross-section types). The history generation unit

44 generates the confidence degree history based on a plurality of confidence degree sets sequentially generated by sequentially analyzing the plurality of input images. The confidence degree for each class can also be referred to as a class probability.

The history evaluation unit 46 evaluates the confidence degree history. By evaluating the confidence degree history, it is possible to determine whether or not the analysis on the input image is appropriate. The history evaluation unit 46 calculates a history evaluation value. Details of a confidence degree history generation method and a confidence degree history evaluation method will be described below. Only the latest confidence degree set may be evaluated. That is, the evaluation value may be calculated based on the latest confidence degree set.

The determination unit 48 is a determiner that determines whether or not to use the external analytic model instead of the analytic model (internal analytic model) 36 based on the evaluation result of the input image, the map evaluation value, and the history evaluation value. That is, the determination unit 48 has a function of selecting the internal analytic model or the external analytic model, and from that viewpoint, the determination unit 48 can be referred to as a selection unit. The determination result of the determination unit 48 is sent to the calculation control unit 30 and a communication unit 50.

The map evaluation value is an evaluation value generated by spatial evaluation. The history evaluation value is an evaluation value generated by temporal evaluation. By simultaneously taking into consideration the two evaluation values, it is possible to accurately determine the necessity of using the external analytic model. However, depending on the situation, only the map evaluation value may be taken into consideration, or only the history evaluation value may be taken into consideration. In the embodiment, since the input image is evaluated, it is possible to avoid the erroneous model performance evaluation caused by the degradation in the quality of the input image.

The communication unit 50 is connected to an information processing apparatus 54 via a network 52. The information processing apparatus 54 includes an analytic model (external analytic model) 56. The analytic model 56 identifies the type of the tomographic image (cross-section type) generated by the ultrasound diagnostic apparatus 10, similar to the analytic model 36 in the ultrasound diagnostic apparatus 10.

The communication unit 50 transfers the input image to the information processing apparatus 54 in a case where the use of the external analytic model has been determined. In that case, a plurality of images constituting the moving image are sequentially transferred, or a still image is transferred. The analytic model 56 analyzes each transferred image and outputs an analysis result for each image. The analysis result is sent from the information processing apparatus 54 to the calculation control unit 30 via the communication unit 50. In a case of the moving image analysis, a series of analysis results are sequentially sent to the calculation control unit 30. In a case of the still image analysis, an analysis result of a specific still image is sent to the calculation control unit 30. As described above, the calculation control unit 30 controls the operation of the ultrasound diagnostic apparatus based on the analysis result of the analytic model 36 or the analysis result of the analytic model 56.

Figure 2:
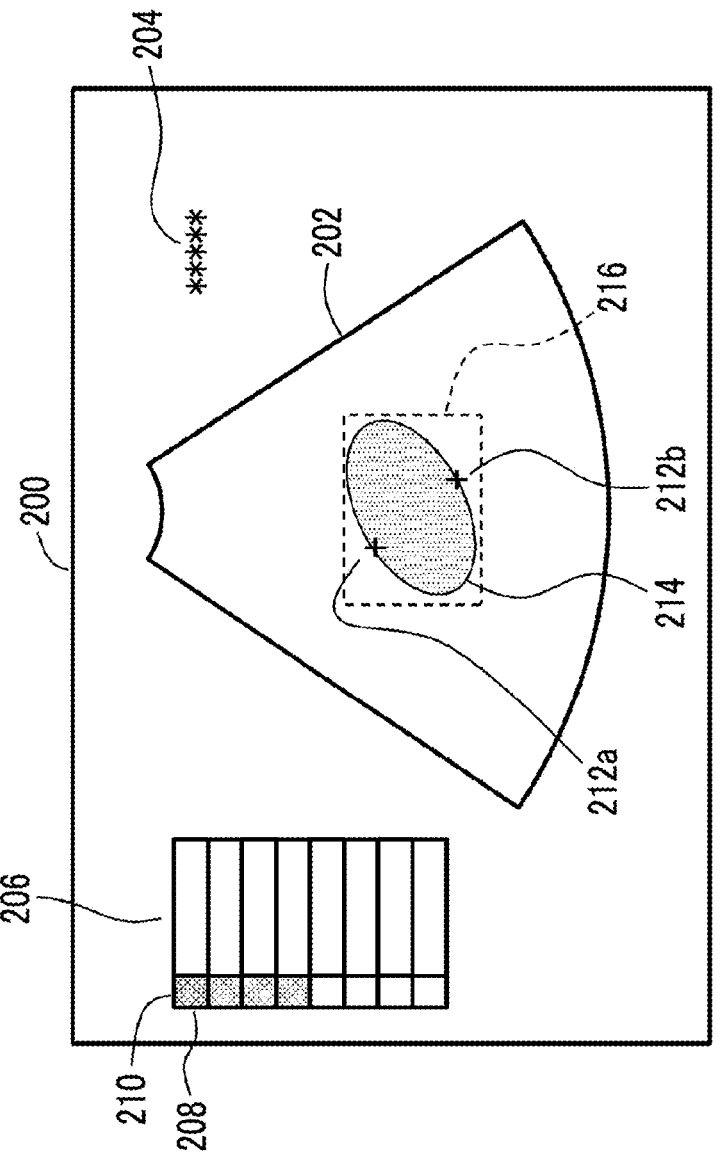
FIG. 2 is a diagram showing a display example.

FIG. 2 shows a display example. An image 200 displayed on the display includes a tomographic image 202. The type of the tomographic image 202, that is, the cross-section type, is identified by the internal analytic model or the external analytic model described above. The identified cross-section type is displayed as text information 204.

The operation of the ultrasound diagnostic apparatus is controlled in accordance with the identified cross-section type. This will be described in detail. In the shown example, the image 200 includes a process list 206 representing a plurality of processes constituting the examination protocol (examination procedure). The process list 206 is composed of a plurality of rows 208 representing the plurality of processes, and each row 208 includes a header or a check field indicating that the process has been executed. The execution of the next process is started at a timing at which the specific cross-section type is identified by the internal analytic model or the external analytic model. For example, a processing condition, a display condition, and the like corresponding to the next process are automatically set in the ultrasound diagnostic apparatus.

The measurement of the tomographic image may be automatically executed based on the identified cross-section type. For example, a series of processing, such as detection of a contour of a tissue 214, setting of two markers 212a and 212b on the contour, and measurement of a distance between the two markers 212a and 212b, may be automatically carried out.

As the analytic model, a model that performs tissue detection may be provided. In that case, a specific tissue (for example, a lesion part) 214 in the tomographic image is automatically detected. In FIG. 2, a box 216 surrounding the specific tissue 214 is displayed.

FIG. 3 organizes differences between the internal analytic model and the external analytic model. For example, the internal analytic model is a model that is suitable for a specific examination site (specific tissue). On the other hand, the external analytic model is a model that is suitable for all the examination sites (or a large number of examination sites). From another perspective, the internal analytic model is a model that can identify a relatively small number of cross sections, and the external analytic model is a model that can identify a significantly large number of cross sections.

For example, the internal analytic model is a model generated through a machine learning process using a relatively small amount of training data, and the external analytic model is a model generated through machine learning using a large amount of training data. The large number of training data may be generated in a large number of medical institutions.

In general, in a case where the internal analytic model is used, better responsiveness can be obtained. On the other hand, in a case where the external analytic model is used, sufficient responsiveness may not be obtained depending on the situation. Additionally, depending on the network conditions, it may be better to avoid the exchange of a large amount of data. In that respect, in the embodiment, basically, the internal analytic model is prioritized for use, and the external analytic model is temporarily or supplementarily used in a case where the internal analytic model cannot perform sufficient analysis. For example, in a case where the internal analytic model cannot perform sufficient analysis on the still image displayed in the frozen state, the still image may be analyzed by the external analytic model.

Figure 4:
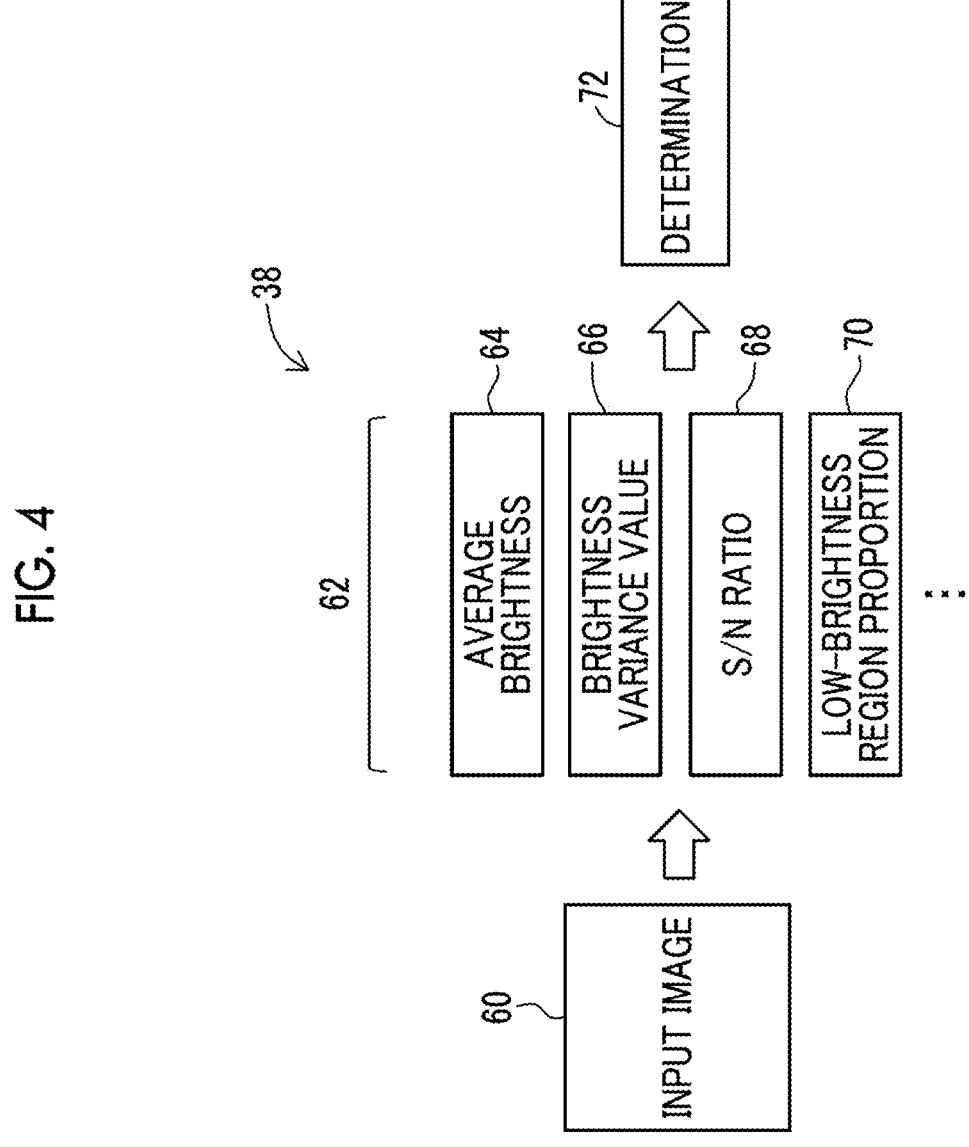
FIG. 4 is a diagram showing an example of an input image evaluation method.

FIG. 4 shows an example of the input image evaluation method. FIG. 4 shows the processing content of the input image evaluation unit 38 shown in FIG. 1.

In FIG. 4, an analysis value set 62 is generated by analyzing an input image 60. In the analysis value set 62, in the shown example, an average brightness 64, a brightness variance value 66, an S/N ratio 68, a low-brightness region proportion 70, and the like are included. For example, in a case where the ultrasound probe is separated from a body surface, the S/N ratio 68 decreases, or the low-brightness region proportion increases. The suitability of the input image 60 is comprehensively determined based on the content of the analysis value set or the changes thereof (refer to reference numeral 72). The evaluation condition to be used may be selected by the user or automatically.

In a case where the quality of the input image is low, a reference image prepared in advance may be displayed. That is, information for supporting the user may be provided to the user such that a high-quality tomographic image is acquired while referring to the displayed reference image.

Figure 5:
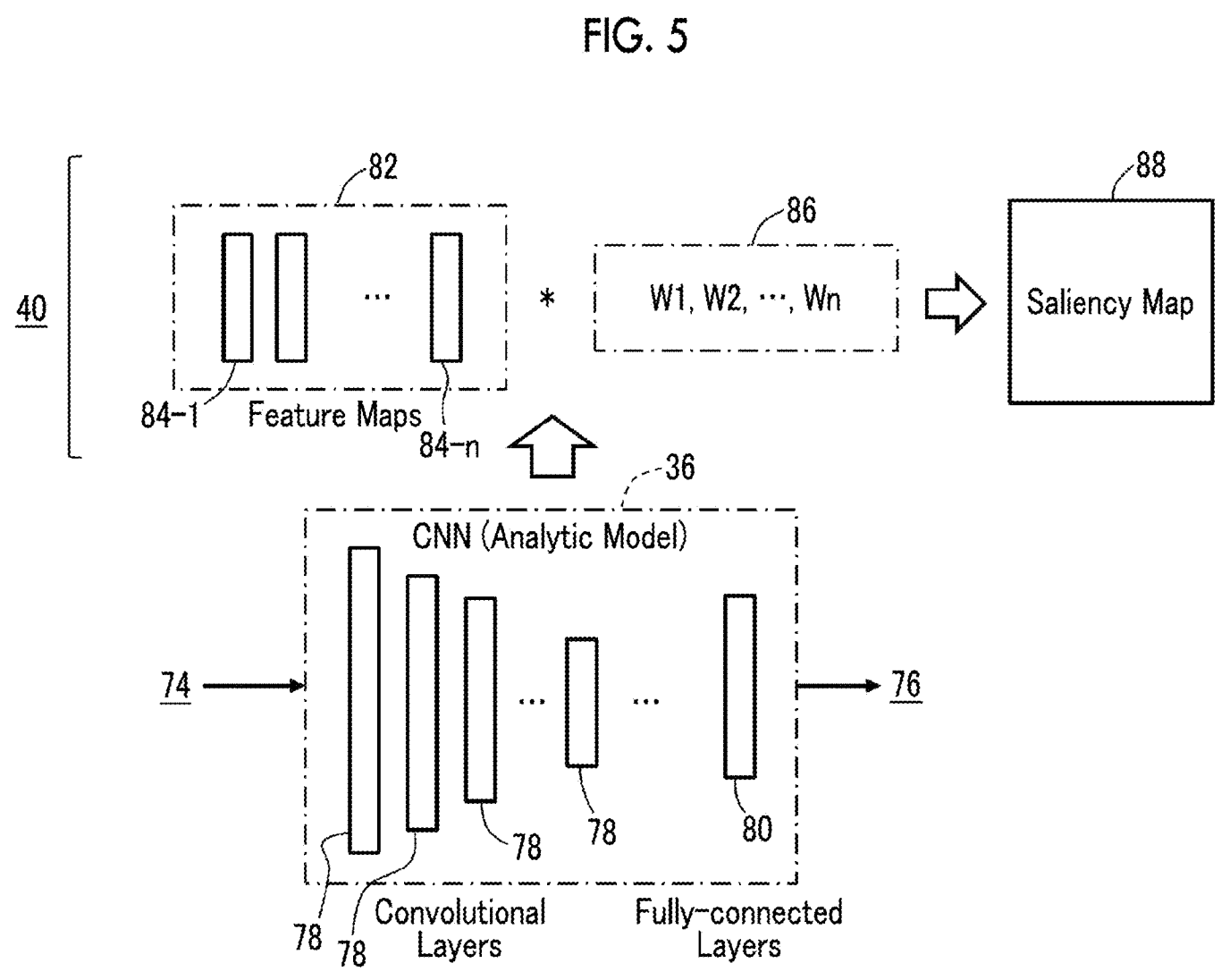

FIG. 5 shows an example of the map generation method. FIG. 5 shows the processing content of the map generation unit 40 shown in FIG. 1.

In FIG. 5, the entity of the analytic model 36 is a CNN. An input image 74 is input to the CNN, and output data 76 is output from the CNN. The CNN includes a plurality of convolutional layers 78. A plurality of feature maps 84-1 to 84-n are generated by the action of the plurality of convolutional layers 78.

In the embodiment, the plurality of feature maps 84-1 to 84-n are extracted from the CNN. The extracted plurality of feature maps 84-1 to 84-n constitute a feature map sequence 82. Each of the feature maps 84-1 to 84-n represents a reaction distribution of each convolutional layer 78. The plurality of feature maps 84-1 to 84-n are multiplied by a plurality of weights 86. A saliency map 88 is generated by adding the plurality of multiplication results.

On the premise that the CNN includes a global average pooling (GAP) layer, the plurality of weights 86 may be extracted from between the GAP layer and a fully-connected layer (output layer) 80 (refer to Zhou et al., Learning Deep Features for Discriminative Localization, arxiv 2015, 1512.04150). The plurality of weights 86 may be calculated by another method. Various existing saliency map generation methods can be used (for example, refer to Selvaraju et al., Grad-CAM: Visual Explanations from Deep Networks via Gradient-based Localization, arxiv 2016, 1610.02391 (Grad-CAM method)). A saliency map corresponding to all the classes may be generated, or a plurality of saliency maps corresponding to a plurality of classes may be individually generated (refer to reference numeral 94).

Figure 6:
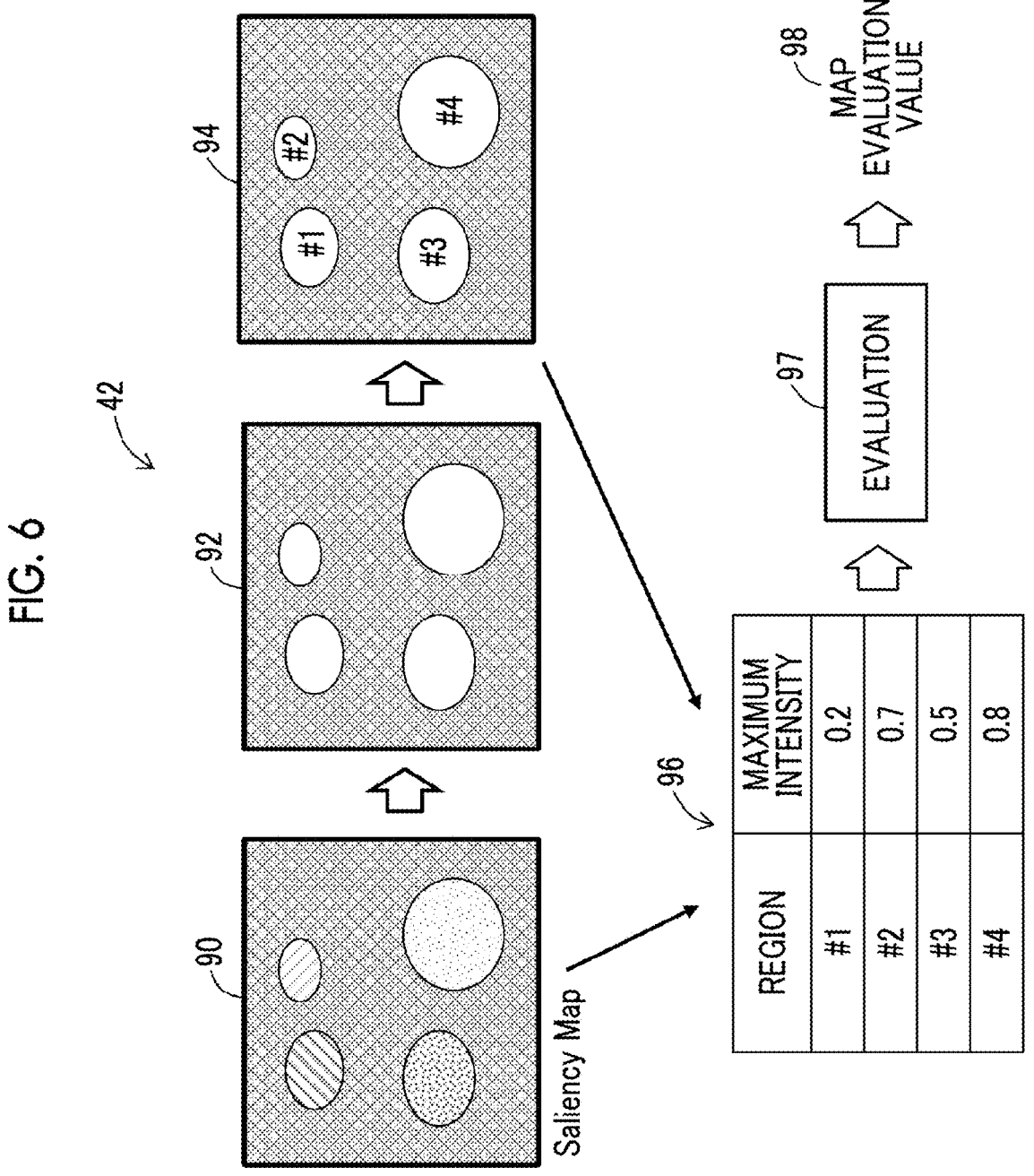
FIG. 6 is a diagram showing an example of a saliency map evaluation method.

FIG. 6 shows an example of the map evaluation method. FIG. 6 shows the processing content of the map evaluation unit 42 shown in FIG. 1.

In the example shown in FIG. 6, binarization processing is applied to a saliency map 90, thereby generating a binarized saliency map 92. Labeling processing or region extraction processing is applied to the binarized saliency map 92, thereby extracting a plurality of regions #1 to #4.

The maximum intensity is specified for each of the regions #1 to #4, thereby generating a table 96. The table 96 includes a plurality of maximum intensities representative of a plurality of regions. One or a plurality of maximum intensities exceeding a threshold value are specified among the plurality of maximum intensities (refer to reference numeral 97), and a map evaluation value 98 is calculated based on the one or plurality of maximum intensities exceeding the threshold value. For example, the map evaluation value may be calculated based on the number of maximum intensities exceeding the threshold value. It is considered that the number indicates spread or strength of the reaction of the CNN. The map evaluation value may be calculated based on the area of each region, the coordinates of each region, and the like.

Figure 7:
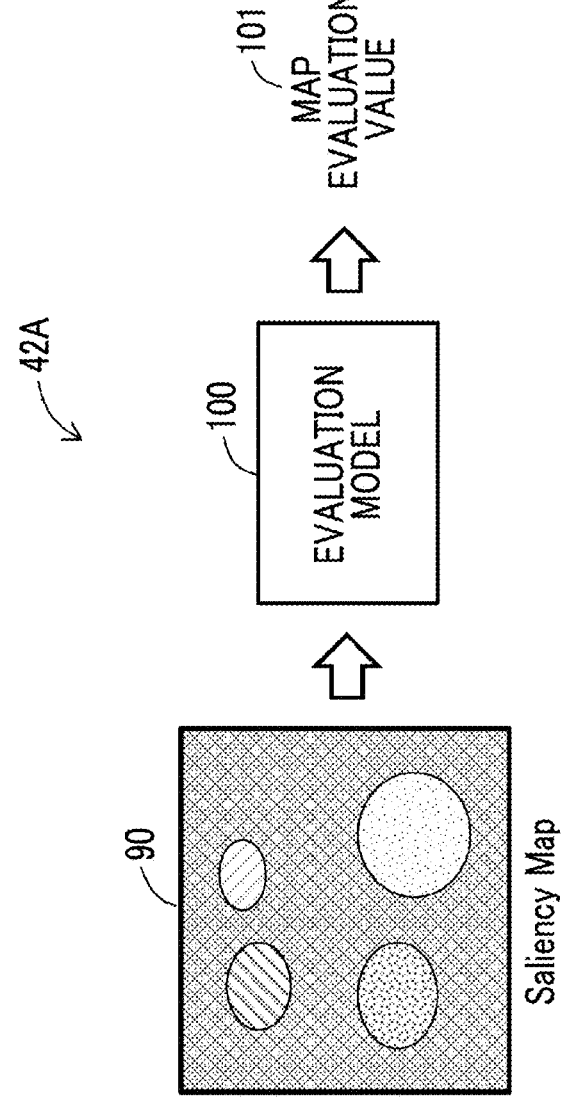
FIG. 7 is a diagram showing another example of the saliency map evaluation method.

FIG. 7 shows another map evaluation method. The saliency map 90 is given to an evaluation model 100 generated through a machine learning process. Consequently, a map evaluation value 101 is output from the evaluation model 100. In a case where the saliency map 90 is analyzed by using the result of the machine learning, it is possible to correctly evaluate the saliency map 90.

Figure 8:
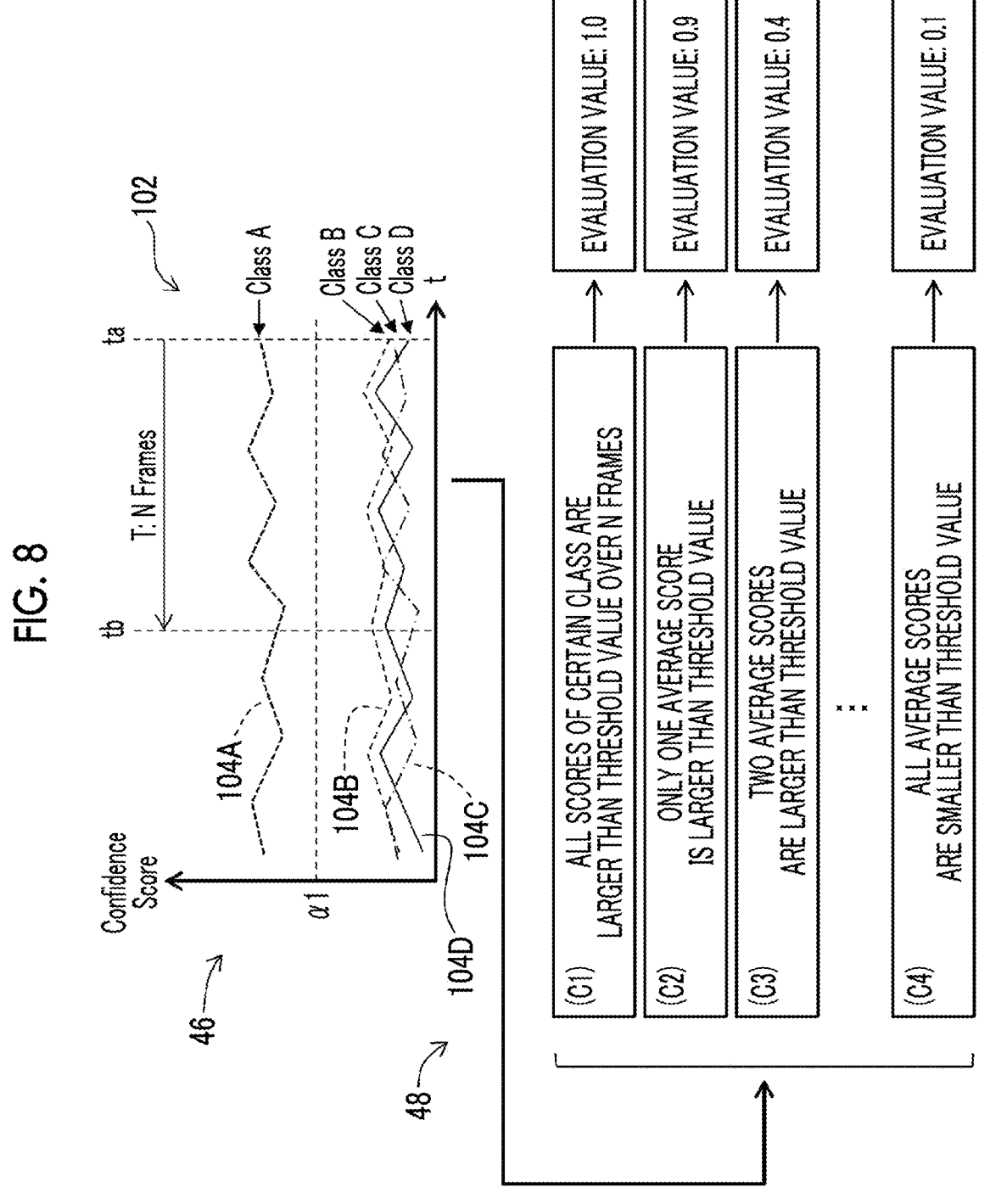
FIG. 8 is a diagram showing a first example of a confidence degree history and an example of a confidence degree history evaluation method.

FIG. 8 shows an example of the confidence degree history and an example of the history evaluation method. FIG. 8 shows the processing content of the history generation unit 44 and the processing content of the history evaluation unit 46 shown in FIG. 1.

In the upper part of FIG. 8, a confidence degree history 102 is composed of a plurality of confidence degree graphs 104A to 104D corresponding to the plurality of classes (the plurality of cross-section types). Each of the confidence degree graphs 104A to 104D consists of a plurality of confidence degrees arranged in a time series. Hereinafter, in some cases, the confidence degree is simply referred to as a score.

A horizontal axis of the confidence degree history 102 is a time axis. ta indicates the current time point, and tb indicates a time point in the past N frames ago. The period between ta and tb is T. For each class, an average value (average score) is calculated from the plurality of confidence degrees within the period T.

The number of frames N to be referred to may vary between a case where the moving image analysis is executed and a case where the still image analysis is executed. The number of frames N to be referred to may be set by the user or automatically depending on the situation. For example, N may be designated from one to several thousand, or T may be designated from several seconds to several hours.

A vertical axis in the confidence degree history 102 indicates the magnitude of the confidence degree. α1 is a threshold value. In the shown confidence degree history 102, only one confidence degree graph 104A exceeds the threshold value α1, and the other confidence degree graphs 104B to 104D are below the threshold value α1.

The evaluation method of the confidence degree history is shown in a lower part of FIG. 8. In the shown example, in a case where the total score of a certain class is larger than the threshold value α1 over N frames (refer to a condition C1), 1.0 is decided on as the evaluation value. In a case where only one average score is larger than the threshold value α1 (refer to a condition C2), 0.9 is decided on as the evaluation value. In a case where both the condition C1 and the condition C2 are satisfied, the satisfaction of the condition C1 is prioritized.

Figure 9:
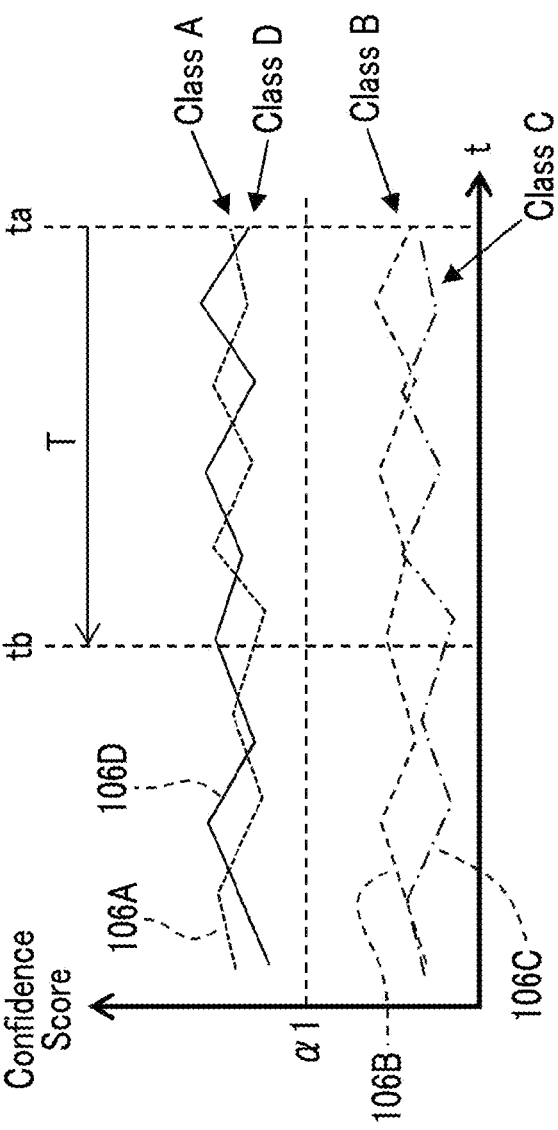
FIG. 9 is a diagram showing a second example of the confidence degree history.

In a case where two average scores are larger than the threshold value α1 (refer to a condition C3), 0.4 is decided on as the evaluation value. This is because it can be said that the narrowing down is insufficient. Such an aspect is shown in FIG. 9. In the confidence degree history shown in FIG. 9, two confidence degree graphs 106A and 106D are larger than the threshold value α1, but the other two confidence degree graphs 106B and 106C are smaller than the threshold value α1.

Figure 10:
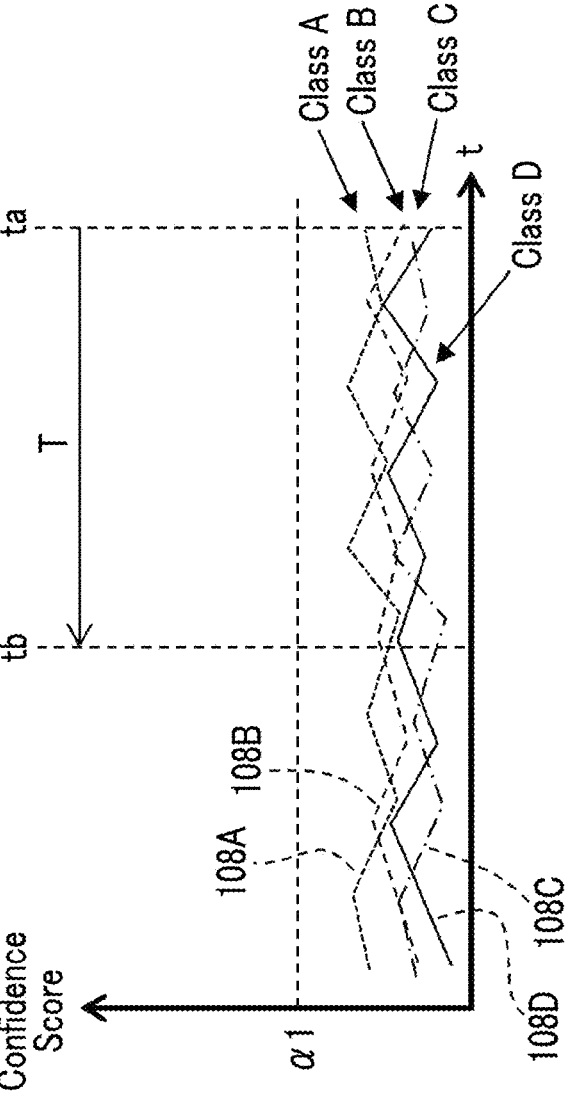
FIG. 10 is a diagram showing a third example of the confidence degree history.

In FIG. 8, in a case where all the average scores are smaller than the threshold value α1, 0.1 is decided on as the evaluation value. Such an aspect is shown in FIG. 10. In the confidence degree history shown in FIG. 10, four confidence degree graphs 108A to 108D are smaller than the threshold value α1.

Figure 11:
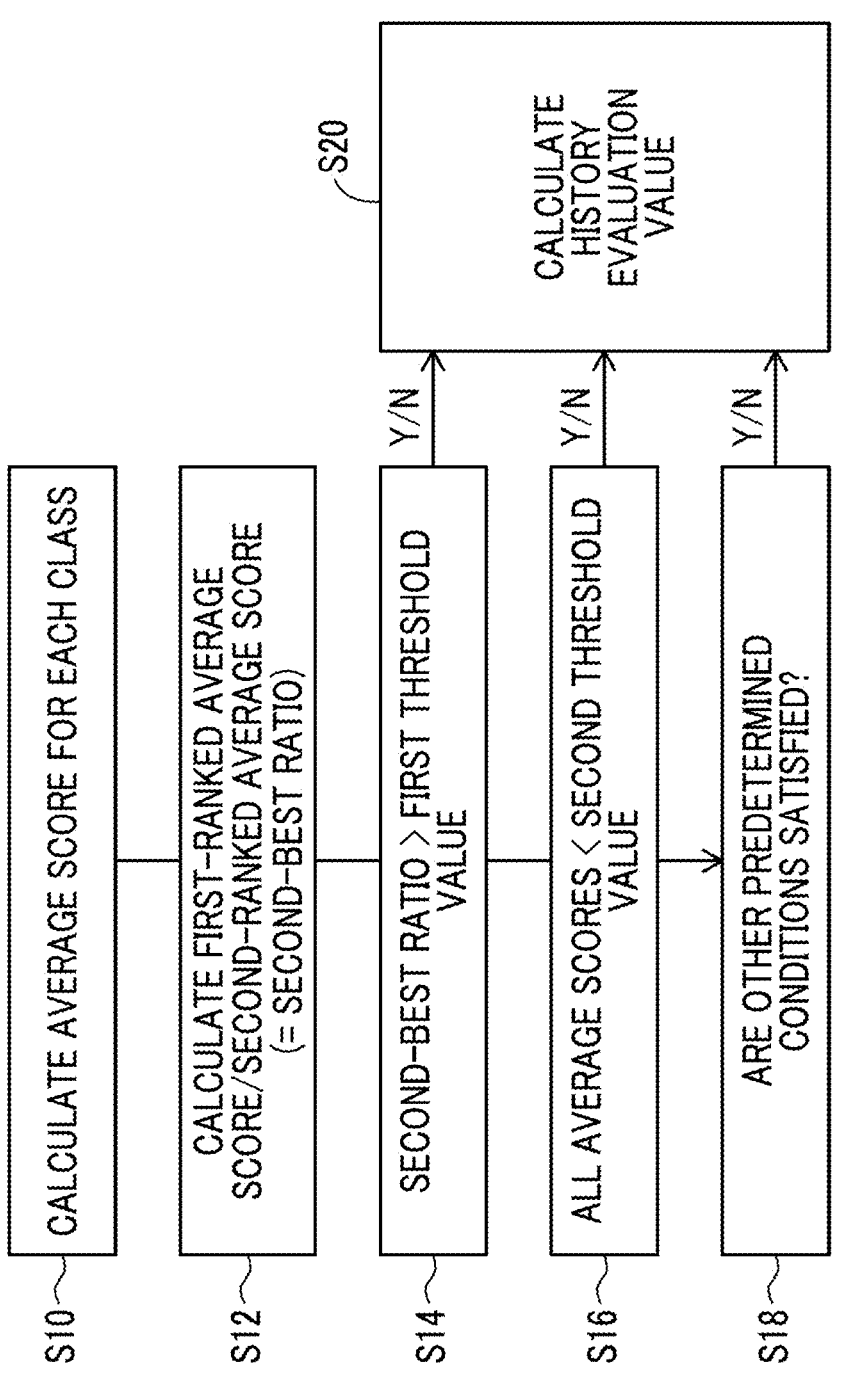
FIG. 11 is a diagram showing another example of the confidence degree history evaluation method.

FIG. 11 shows another evaluation method of the confidence degree history. In S10, the average score is calculated for each class within a certain period. In S12, the second-best ratio is calculated by dividing the first-ranked average score (the largest average score) by the second-ranked average score (the second largest average score).

In S14, it is determined whether or not the second-best ratio is larger than a first threshold value. In S16, it is determined whether or not all the average scores are smaller than a second threshold value. In S18, it is determined whether or not other predetermined conditions are satisfied.

In S20, the history evaluation value is calculated based on a determination result in S14, a determination result in S16, and a determination result in S18. Various operation methods can be employed in the operation. Examples of other predetermined conditions applied in S18 include a condition related to temporal stability of each score. The evaluation methods shown in FIGS. 8 and 11 are examples, and various evaluation methods can be employed.

FIG. 12 shows the processing content of the determination unit (selection unit) 48 shown in FIG. 1. The presence or absence of the use of the external analytic model is determined based on an input image evaluation result 110, a map evaluation value 112, and a history evaluation value 114. That is, the internal analytic model or the external analytic model is selected as a target for the use (refer to reference numeral 115). Reference numeral 118 indicates the selection of the external analytic model, and reference numeral 120 indicates the selection of the internal analytic model.

In the embodiment, the external analytic model is selected, in a case where the quality of the input image satisfies a predetermined input image quality condition, and the map evaluation value and the history evaluation value do not satisfy a predetermined model performance condition. In that case, it may be determined that the predetermined model performance condition is satisfied in a case where at least one of the map evaluation value or the history evaluation value exceeds a predetermined threshold value. Alternatively, it may be determined that the predetermined model performance condition is satisfied in a case where both the map evaluation value and the history evaluation value exceed the predetermined threshold value. Depending on the situation, only one of the map evaluation value or the history evaluation value may be referred to. In a case where the quality of the input image does not satisfy the predetermined input image quality condition, the selection of the model is not executed, and the control based on the analysis result is temporarily stopped (refer to reference numeral 116). In this case, a message representing the degradation in image quality may be provided to the user.

In the embodiment, even in a situation in which the external analytic model is being used, the internal analytic model is operating, and the performance of the internal analytic model is continuously evaluated. The determination unit 48 determines the resumption of the use of the internal analytic model at a time point when the quality of the input image satisfies the predetermined input image quality condition, and the map evaluation value and the history evaluation value satisfy the predetermined model performance condition (refer to reference numeral 115).

FIG. 13 shows an ultrasound diagnostic system according to another embodiment. An ultrasound diagnostic apparatus 121 is connected to a network 122. Information processing apparatuses 124 and 126 are connected to the network 122. The ultrasound diagnostic apparatus 121 includes an internal analytic model 128 and a model selection unit 130. The information processing apparatus 124 includes a first external analytic model 132. The information processing apparatus 126 includes a second external analytic model 134.

The internal analytic model 128, the first external analytic model, and the second external analytic model each identify the type of the tomographic image generated in the ultrasound diagnostic apparatus. The model selection unit 130 selects the analytic model to be used, based on the evaluation result of the performance of the internal analytic model 128. Specifically, the model selection unit 130 selects whether to use the internal analytic model 128 or to use the external analytic model, and selects whether to use the first external analytic model 132 or to use the second external analytic model 134 in a case of using the external analytic model. The model selection unit 130 may select the external analytic model to be used, in accordance with the content or the quality of the tomographic image. The external analytic model to be used may be selected based on the performance and the track record of the first external analytic model 132, and the performance and the track record of the second external analytic model 134.

A plurality of internal analytic models may be provided inside the ultrasound diagnostic apparatus, and the plurality of internal analytic models may be selectively used. In that case as well, an analytic model selection technique according to the embodiment can be applied.

What is claimed is:

1. An ultrasound diagnostic apparatus used in an ultrasound examination of a subject, the ultrasound diagnostic apparatus comprising:
   a generator that generates an ultrasound image based on data obtained from the subject;
   an internal analytic model that is provided inside the ultrasound diagnostic apparatus and analyzes the ultrasound image;
   an evaluator that evaluates the internal analytic model;
   a determiner that determines use of an external analytic model based on an evaluation result of the evaluator, wherein the external analytic model is located on an information processing apparatus connected to the ultrasound diagnostic apparatus via a network, each of the internal analytic model and the external analytic model is a model generated through a machine learning process and used to identify a type of the ultrasound image or detect a lesion part included in the ultrasound image, and the internal analytic model is a subset of the external analytic model and has a scale smaller than a scale of the external analytic model; and
   a communicator that transfers the ultrasound image to the external analytic model in response to the use of the external analytic model being determined, and that receives an analysis result of the external analytic model,
   wherein the evaluator includes
   a map generator that generates a saliency map representing a reaction distribution of the internal analytic model based on a plurality of feature maps extracted from a plurality of convolutional layers of the internal analytic model, and
   a map evaluator that evaluates whether or not an analysis result of the internal analytic model is appropriate based on a number or a distribution of a plurality of high intensities in the saliency map, and
   the determiner determines the use of the external analytic model based on an evaluation result of the saliency map.

2. The ultrasound diagnostic apparatus according to claim 1,
   wherein the evaluator evaluates the internal analytic model based on at least one of internal data extracted from the internal analytic model or output data output from the internal analytic model.

3. The ultrasound diagnostic apparatus according to claim 2,
   wherein the evaluator evaluates the internal analytic model based on both the internal data and the output data.

4. The ultrasound diagnostic apparatus according to claim 1,
   wherein the evaluator includes
   a history generator that generates a confidence degree history representing temporal changes of confidence degrees for a plurality of classes based on output data output from the internal analytic model, and
   a history evaluator that evaluates the confidence degree history, and
   the determiner determines the use of the external analytic model based on an evaluation result of the confidence degree history.

5. The ultrasound diagnostic apparatus according to claim 1, further comprising:
   an input image evaluator that evaluates an input image, which is an ultrasound image input to the internal analytic model,
   wherein the determiner determines the use of the external analytic model based on an evaluation result of the input image.

6. The ultrasound diagnostic apparatus according to claim 5,
   wherein the determiner determines the use of the external analytic model, in response to the input image satisfying an image quality condition, and an evaluation result of the internal analytic model not satisfying a model performance condition.

7. The ultrasound diagnostic apparatus according to claim 1, further comprising:
   a controller that controls an operation of the ultrasound diagnostic apparatus,
   wherein the internal analytic model and the external analytic model are each a model that identifies a cross section, and
   the controller controls the operation of the ultrasound diagnostic apparatus based on the cross section identified by the internal analytic model until the use of the external analytic model is determined, and controls the operation of the ultrasound diagnostic apparatus based on the cross section identified by the external analytic model after the use of the external analytic model has been determined.

8. The ultrasound diagnostic apparatus according to claim 1,
   wherein the evaluator continues to evaluate the internal analytic model even after the use of the external analytic model has been determined, and
   the determiner determines resumption of use of the internal analytic model based on the evaluation result of the evaluator after the use of the external analytic model has been determined.

9. An ultrasound diagnostic system comprising:
   an ultrasound diagnostic apparatus used in an ultrasound examination of a subject; and
   an information processing apparatus connected to the ultrasound diagnostic apparatus via a network,

wherein the information processing apparatus includes an external analytic model that analyzes an ultrasound image outside the ultrasound diagnostic apparatus, and the ultrasound diagnostic apparatus includes a generator that generates the ultrasound image based on data obtained from the subject, an internal analytic model that analyzes the ultrasound image inside the ultrasound diagnostic apparatus, an evaluator that evaluates the internal analytic model, a determiner that determines use of the external analytic model, based on an evaluation result of the evaluator, wherein each of the internal analytic model and the external analytic model is a model generated through a machine learning process and used to identify a type of the ultrasound image or detect a lesion part included in the ultrasound image, and the internal analytic model is a subset of the external analytic model and has a scale smaller than a scale of the external analytic model, and

a communicator that transfers the ultrasound image to the external analytic model in response to the use of the external analytic model being determined, and that receives an analysis result of the external analytic model, wherein the evaluator includes a map generator that generates a saliency map representing a reaction distribution of the internal analytic model based on a plurality of feature maps extracted from a plurality of convolutional layers of the internal analytic model, and a map evaluator that evaluates whether or not an analysis result of the internal analytic model is appropriate based on a number or a distribution of a plurality of high intensities in the saliency map, and the determiner determines the use of the external analytic model based on an evaluation result of the saliency map.

* * * * *